(12) United States Patent
Yasuda et al.

(10) Patent No.: US 10,493,013 B2
(45) Date of Patent: Dec. 3, 2019

(54) LIQUID SKIN-CONDITIONING COMPOSITION

(71) Applicant: SHISEIDO COMPANY, LTD., Tokyo (JP)

(72) Inventors: Chihiro Yasuda, Yokohama (JP); Kazunobu Suzuki, Yokohama (JP)

(73) Assignee: SHISEIDO COMPANY, LTD., Tokyo (JP)

(*) Notice: Subject to any disclaimer, the term of this patent is extended or adjusted under 35 U.S.C. 154(b) by 0 days.

(21) Appl. No.: 15/264,122

(22) Filed: Sep. 13, 2016

(65) Prior Publication Data

US 2016/0374923 A1 Dec. 29, 2016

Related U.S. Application Data

(62) Division of application No. 14/236,348, filed as application No. PCT/JP2012/067729 on Jul. 11, 2012, now abandoned.

(30) Foreign Application Priority Data

Aug. 5, 2011 (JP) ................. 2011-171548

(51) Int. Cl.
*A61K 8/73* (2006.01)
*A61K 8/44* (2006.01)
*A61Q 19/00* (2006.01)
*A61Q 19/02* (2006.01)

(52) U.S. Cl.
CPC ............ *A61K 8/731* (2013.01); *A61K 8/44* (2013.01); *A61Q 19/00* (2013.01); *A61Q 19/007* (2013.01); *A61Q 19/02* (2013.01)

(58) Field of Classification Search
None
See application file for complete search history.

(56) References Cited

U.S. PATENT DOCUMENTS

2010/0035831 A1* 2/2010 Matsunaga ............ A61K 8/604
514/25

FOREIGN PATENT DOCUMENTS

| | | |
|---|---|---|
| CN | 101925353 | 12/2010 |
| CN | 102238934 | 11/2011 |
| JP | 1-93519 | 4/1989 |
| JP | 7-233042 | 9/1995 |
| JP | 9-263510 | 10/1997 |
| JP | 10-265323 | 10/1998 |
| JP | 2002-284664 | 10/2002 |
| JP | 2006-8615 | 1/2006 |
| JP | 2006-265140 | 10/2006 |
| JP | 2010-116392 | 5/2010 |
| WO | WO 2009/093534 | 7/2009 |
| WO | WO 2010/001926 | 1/2010 |
| WO | WO 2010/044261 | 4/2010 |
| WO | WO 2010/064578 | 6/2010 |

OTHER PUBLICATIONS

CN 201280037410.2 Office Action dated Jul. 14, 2014, 6 pages—English; 9 pages—Japanese.
PCT/JP2012/067729 International Search Report, 2 pages—English; 3 pages—Japanese.

* cited by examiner

*Primary Examiner* — David J Blanchard
*Assistant Examiner* — Sarah J Chickos
(74) *Attorney, Agent, or Firm* — Andrew F. Young, Esq.; Lackenbach Siegel, LLP

(57) ABSTRACT

The present invention provides an external-use liquid skin-conditioning composition that not only reduces the sticky and friction sensations caused by the inclusion of tranexamic acid, but also has a rich body without feeling slimy and softens the skin after use. The composition comprises (A) 0.5 to 5 mass % of at least one item selected from a group consisting of tranexamic acid and derivatives thereof and (B) 0.005 to 1.5 mass % of carboxymethylcellulose, has a viscosity of no greater than 500 mPa s at 30° C., and is transparent or semitransparent with an L value between 50 and 100 inclusive. Preferably the composition contains only carboxymethylcellulose as a thickener.

4 Claims, No Drawings

LIQUID SKIN-CONDITIONING COMPOSITION

TECHNICAL FIELD

The present invention relates to a liquid skin-conditioning composition, which contains tranexamic acids, does not cause stickiness or coarseness, and offers a rich texture without sliminess and softness after application.

BACKGROUND ART

Tranexamic acids have an antiplasmin action and are added to various cosmetic products as active components for improving rough skin, whitening, and the like. Further, a synergistic effect and a novel effect of a combination of tranexamic acids and other substances are also found, and Patent Document 1, for example, describes a skin-conditioning agent which contains at least two components selected from tranexamic acid, arbutin, trimethylglycine, and vitamin E and prevents the skin dullness caused by various factors.

Also, Patent Document 2 states that, in emulsion cosmetics (creams and milky lotions) to which an oil component is added to provide skin improving effects, an emulsion composition which is stable over an extended period of time without additionally containing a common surfactant while maintaining a refreshing sensation when used can be obtained by adding an alkyl-modified carboxy vinyl polymer and tranexamic acid.

However, cosmetics, particularly low viscosity cosmetics such as a skin softener, to which tranexamic acids are added, pose a problem of causing stickiness and coarseness from adding tranexamic acids, and Patent Document 3 states that the stickiness and coarseness are suppressed when a predetermined amount of xanthan gum is added.

CITATION LIST

Patent Document

Patent Document 1: Japanese Patent Laid-Open No. 10-265323
Patent Document 2: Japanese Patent Laid-Open No. 9-263510
Patent Document 3: Japanese Patent Laid-Open No. 2010-116332

SUMMARY OF INVENTION

Technical Problem

In transparent low viscosity liquid composition such as skin softeners, the stickiness from tranexamic acids can be suppressed to some extent by adding xanthan gum; however, the effect therefrom is not always sufficient and the addition of a thickener such as xanthan gum or (alkyl-modified) carboxy vinyl polymer posed a problem of causing cloudiness and sliminess. Further, another problem was also raised in that the color of appearance discolors over time when tranexamic acid and xanthan gum were added together.

Accordingly, an object of the present invention is to provide a liquid skin-conditioning composition, which not only suppresses the stickiness and coarseness caused by adding tranexamic acids but also offers a rich texture without sliminess and the skin softness after application, and is free from the discoloration over time.

Solution to Problem

To solve the above problems, the present inventors carried out extensive studies and found that a liquid skin-conditioning composition, which can suppress the stickiness and coarseness caused by tranexamic acids, achieve a rich texture without sliminess, and has a smooth and dry feel when used, is obtained when carboxymethylcellulose is added as a thickener to a composition containing tranexamic acids, whereby the present invention was accomplished.

More specifically, the present invention provides a liquid skin-conditioning composition containing (A) 0.5 to 5% by mass of at least one selected from the group consisting of tranexamic acid and derivatives thereof, and (B) 0.005 to 1.5% by mass of carboxymethylcellulose, having a viscosity of 500 mPa·s or less at 30° C., and being transparent or semitransparent with an L value of 50 or more and 100 or less.

Advantageous Effects of Invention

The liquid skin-conditioning composition of the present invention, even when containing tranexamic acids, has a good feel of use wherein the stickiness and coarseness caused thereby are suppressed, a rich texture without sliminess is achieved, and a smooth and dry feel and the skin softness are provided.

DESCRIPTION OF EMBODIMENTS

The liquid skin-conditioning composition according to the present invention is a transparent or semitransparent liquid composition represented by a skin softener and applied to the skin surface. The skin softener typically refers to those in which a water insoluble substance is solubilized and thermodynamically stabilized to give a transparent liquid appearance, but the liquid skin-conditioning composition of the present invention encompasses, in addition to the above transparent soluble type, transparent or semitransparent skin softeners which adopt the microemulsion or lipid nanosphere technologies and skin softener type transparent or semitransparent essences (beauty essences).

Also, the skin-conditioning composition of the present invention is a water-base low viscosity liquid composition having a viscosity, at 30° C., of 500 mPa·s or less, preferably 450 mPa·s or less, more preferably 400 mPa·s or less. Here, the viscosity in the present specification is the value measured with a VDA viscometer (Shibaura Systems Co., LTD., DIGITAL VISMETRON VDA), using Rotor No. 1 or No. 2, under the conditions of a number of revolutions of 12 rpm and 1 minute.

The skin-conditioning composition of the present invention is preferably a transparent or semitransparent liquid composition. The "transparent or semitransparent" used in the present specification means those having an L value of 50 or more and 100 or less, of which the "transparent" means those having an L value of 98 or more. The L value is the criterion indicating a turbidity degree of a composition, and refers to a transparency degree of a composition measured when the transparency degree at which the light is transmitted through a glass cell containing purified water is defined as 100, whereas when the transparency degree at which the light is completely blocked and no light is transmitted is defined as 0. The transparency degree, i.e., the L value, can be measured, for example, using a known color difference meter such as Color-EYE7000 (product of GretagMacbeth GmbH) or a known spectrophotometer. The composition of the present invention has such an L value of 50 or more, preferably 60 or more, more preferably 70 or more, and, for example, cloudy emulsion type compositions containing a large amount (10% by mass or more) of an oil component are not encompassed.

The composition of the present invention contains at least one (component A) selected from tranexamic acids and the derivatives thereof (hereinafter referred to as "tranexamic acids"). Tranexamic acid (trans-4-aminomethylcyclohexane-1-carboxylic acid) and the derivatives thereof are commonly used as an antiplasmin agent and known as very safe components to be used as a skin-conditioning agent such as cosmetic products.

The tranexamic acids contained in the composition of the present invention may be those conventionally used in cosmetic products and the like, without particularly being limited, and examples include, also in the form of derivatives thereof in addition to tranexamic acids, tranexamates (metal salts such as magnesium salt, calcium salt, sodium salt, and potassium salt, phosphate, hydrochloride, hydrobromide, sulfate, and the like), amides of the tranexamic acids (methyl amide or salts thereof, and the like), and dimers of the tranexamic acids.

The amount of the tranexamic acids to be added in the composition of the present invention is 0.5 to 5.0% by mass, preferably 1.0 to 3.0% by mass, more preferably 1.0 to 2.0% by mass. When the amount is below 0.5% by mass, the effects rendered by tranexamic acids (rough skin improvement, whitening, and the like) are not fully achieved, whereas when the amount exceeding 5.0% by mass is added, the suppression of stickiness may sometimes be difficult.

The composition of the present invention contains carboxymethylcellulose (component B), in addition to the tranexamic acids. Carboxymethylcellulose is a cellulose water soluble polymer conventionally added to cosmetic products and the like, as a kind of thickener. In the present invention, the carboxymethylcellulose having an average polymerization degree of about 150 to about 500 (average molecular weight of about 30,000 to about 120,000) is used preferably. The etherification degree of carboxymethylcellulose is not particularly limited and typically about 0.55 to 0.80. For example, a commercial product such as Cellogen PR (trade name: product of DAI-ICHI KOGYO SEIYAKU CO., LTD.; average polymerization degree of 220 to 250, average molecular weight of 47,000 to 54,000) can also be used.

The amount of carboxymethylcellulose to be added in the composition of the present invention is 0.005 to 1.5% by mass, preferably 0.01 to 0.5% by mass, more preferably 0.02 to 0.1% by mass. When the amount is below 0.005% by mass, the stickiness and coarseness caused by tranexamic acids may not be fully suppressed sometimes, whereas when the amount exceeding 1.5% by mass is contained, the sliminess and stickiness caused by carboxymethylcellulose may sometimes occur.

In the composition of the present invention, the stickiness and sliminess from thickeners may be caused or the transparency degree may be deteriorated sometimes when other thickeners such as xanthan gum, carboxy vinyl polymer, or alkyl-modified carboxy vinyl polymer are added. Thus, the composition of the present invention preferably contains only carboxymethylcellulose as a thickener but not any other thickeners.

The composition of the present invention may contain other optional components typically added to skin softeners, essences (beauty essences), and the like.

Examples of the optional component include water, alcohols, moisturizers, softeners (emollient agents), surfactants (solubilizing agents, emulsifiers), drugs, buffers, perfumes, coloring agents, and preservatives.

The composition of the present invention is a water-base low viscosity liquid composition, and thus water accounts for the majority of the composition with the amount thereof to be added typically being 30 to 95% by mass, preferably 50 to 90% by mass.

For the moisturizer, polyhydric alcohols such as glycerin, dipropylene glycol, and butylene glycol are preferable, with the amount thereof to be added typically being about 0.1 to 30% by mass, preferably 0.5 to 15% by mass.

The surfactant (solubilizing agent) is preferably a hydrophilic amphiphilic substance, and the absorbability to the skin when the composition is applied can further be improved by containing it.

Examples of the hydrophilic amphiphilic substance contained in the composition of the present invention may be those used conventionally in cosmetic products and the like, without being particularly limited, and examples include polyoxyethylene fatty acid ether, polyoxyethylene fatty acid ester, polyoxyethylene alkyl ether, polyoxyethylene polyoxypropylene alkyl ether, polyoxyethylene alkyl phenyl ether, polyoxyethylene cholesteryl ether, polyoxyethylene phytosterol ether, polyoxyethylene polyoxypropylene phytosterol ether, polyoxyethylene hydrogenated castor oil, polyoxyethylene sorbitan fatty acid ester, polyoxyethylene sorbitol fatty acid ester, polyoxyethylene fatty acid glycerin, polyglycerin fatty acid ester, sucrose fatty acid ester, fatty acid soap, N-acyl glutamate, acyl taurine salt, acyl alkyl taurine salt, higher alkyl sulfate ester, alkyl ether sulfate ester, N-acyl sarcosinate, higher fatty acid amide sulfonate, phosphate ester, sulfosuccinate, alkylbenzene sulfonates, polyoxyethylene methyl ether dimethicone, and polyoxyethylene-methyl polysiloxane.

Of these, it is particularly preferable to use at least one selected from polyoxyethylene polyoxypropylene alkyl ether, polyoxyethylene hydrogenated castor oil, polyoxyethylene phytosterol ether, and polyoxyethylene-methyl polysiloxane.

The content of the hydrophilic amphiphilic substance in the composition of the present invention is not particularly limited, but preferably 0.01 to 1.0% by mass, more preferably 0.05 to 0.3% by mass. The content of less than 0.01% by mass is not sufficient to improve the absorbability to the skin, whereas the content exceeding 1.0% by mass may rather cause stickiness.

The softener (emollient agent) is preferably an oil component which is in the form of liquid at ordinary temperature, and the moistness and skin softness when the composition is applied can further be improved by adding it.

The liquid oil component added to the composition of the present invention may be those conventionally used in cosmetic products and the like, without being particularly limited, and, for example, those conventionally used in cosmetic products and the like, such as oils and fats, fatty acids, ester oils, hydrocarbon oil, higher alcohols, or silicone oils, may be used. Specific examples include those listed below.

Examples of the oils and fats include flaxseed oil, camellia oil, macadamia nut oil, corn oil, olive oil, avocado oil, sasanqua oil, castor oil, safflower oil, apricot kernel oil, cinnamon oil, jojoba oil, grape oil, sunflower seed oil, almond oil, rapeseed oil, sesame oil, wheat germ oil, rice germ oil, rice bran oil, cotton seed oil, soybean oil, peanut oil, tea oil, and evening primrose oil.

Examples of the fatty acid include heptanoic acid, octanoic acid, nonanoic acid, decanoic acid, pentadecanoic acid, heptadecanoic acid, nonadecanoic acid, isostearic acid, oleic acid, linolic acid, linolenic acid, and arachidonic acid.

Examples of the ester oil include pentaerythrite tetraoctanoate, cetyl octanoate, hexyl laurate, isopropyl myristate, octyldodecyl myristate, octyl palmitate, isopropyl isostearate, octyl isopalmitate, isodecyl oleate, and cetyl ethylhexanoate.

Examples of the hydrocarbon oils include liquid paraffin, squalane, squalene, paraffin, isoparaffin, octane, decane, dodecane, isododecane, hexadecane, and isohexadecane.

Examples of the higher alcohol include octyl alcohol, isostearyl alcohol, and oleyl alcohol.

Examples of the silicone oil include chain silicones such as dimethylpolysiloxane, methylphenyl polysiloxane, and methyl hydrogen polysiloxane, and cyclic silicones such as octamethylcyclotetrasiloxane, decamethylcyclopentasiloxane, and dodecamethylcyclohexasiloxane.

In addition, in the case where a liquid oil component is contained, it is preferably to coexist with the above hydrophilic amphiphilic substance, and coexistence thereof enhances the solubilization stability or emulsion stability of the liquid oil component.

The amount of the liquid oil component to be added in the composition of the present invention is not particularly limited, but preferably 0.01 to 10.0% by mass, more preferably 0.05 to 5.0% by mass. The content of less than 0.01% by mass is not sufficient to improve the moistness and skin softness, whereas the content exceeding 10.0% by mass may cause stickiness sometimes due to the increased amount of the hydrophilic amphiphilic substance or the like, which needs to be added for the stable addition thereof.

EXAMPLES

Hereinafter, the present invention is further described in details with reference to specific examples, which do not, however, limit the technical scope of the present invention. The amount in formulae in the following Examples, Comparative Examples, and Formulation Examples are shown in % by mass.

Examples 1 to 6, Comparative Examples 1 to 5

The liquid compositions (solubilized type) having the composition shown in Tables 1 to 3 below were prepared.

Subsequently, the actual application test using these compositions was carried out by 20 specialist panelists. Test items include stickiness, freshness, rich texture, skin softness, smooth and dry feel, sliminess, and appearance change (discoloration) over time. Each test item was evaluated by each specialist panelist in accordance with the following evaluation score criteria, and ranked into four levels based on the total of evaluation scores. The appearance change (discoloration) over time was also evaluated in accordance with the following evaluation criteria according to the degree of discoloration. The ranked results are shown together in Tables 1 to 3.

Evaluation Score Criteria (Stickiness, Freshness, Rich Texture, Skin Softness, Smooth and Dry Feel, and Sliminess):
  5 Points: superior
  4 Points: excellent
  3 Points: fair
  2 Points: poor
  1 Point: very poor Evaluation Ranks:
  A: total point is 80 or more
  B: total point is 60 or more and below 80
  C: total point is 40 or more and below 60
  D: total point is below 40

Evaluation Criteria; Appearance Change (Discoloration) Over Time:
  A: same as the standard product (no discoloration)
  B: slightly discolored
  D: notably discolored

TABLE 1

| Name of raw materials | Comparative Example 1 | Comparative Example 2 | Comparative Example 3 |
|---|---|---|---|
| Purified water | Balance | Balance | Balance |
| Ethanol | 4 | 4 | 4 |
| Glycerin | 3 | 3 | 3 |
| Dipropylene glycol | 5 | 5 | 5 |
| PEG/PPG-14/7 dimethyl ether | 3 | 3 | 3 |
| Xanthan gum | — | — | 0.02 |
| Carboxymethyl-cellulose | — | — | — |
| PPG-13 decyltetradeceth-24 | 0.2 | 0.2 | 0.2 |
| Tranexamic acid | — | 2 | 2 |
| Citric acid | Proper quantity | Proper quantity | Proper quantity |
| Sodium citrate | Proper quantity | Proper quantity | Proper quantity |
| Disodium edetate | Proper quantity | Proper quantity | Proper quantity |
| Na pyrosulfite | Proper quantity | Proper quantity | Proper quantity |
| Phenoxy ethanol | Proper quantity | Proper quantity | Proper quantity |
| Perfume | Proper quantity | Proper quantity | Proper quantity |
| Total | 100 | 100 | 100 |
| Absence of stickiness when drying | B | D | C |
| Freshness | D | B | B |
| Rich texture | D | D | B |
| Skin softness | D | D | C |
| Smooth and dry feel | D | D | D |
| Sliminess | B | B | D |
| Appearance (color) over time | A | B | D |
| Viscosity (mPa · s) | 10 | 10 | 10 |

TABLE 2

| Name of raw materials | Example 1 | Example 2 | Example 3 | Example 4 | Example 5 | Comparative Example 4 |
|---|---|---|---|---|---|---|
| Purified water | Balance | Balance | Balance | Balance | Balance | Balance |
| Ethanol | 4 | 4 | 4 | 4 | 4 | 4 |
| Glycerin | 3 | 3 | 3 | 3 | 3 | 3 |
| Dipropylene glycol | 5 | 5 | 5 | 5 | 5 | 5 |
| PEG/PPG-14/7 dimethyl ether | 3 | 3 | 3 | 3 | 3 | 3 |

TABLE 2-continued

| Name of raw materials | Example 1 | Example 2 | Example 3 | Example 4 | Example 5 | Comparative Example 4 |
|---|---|---|---|---|---|---|
| Carboxymethylcellulose | 0.01 | 0.05 | 0.1 | 1 | 1.5 | 2 |
| PPG-13 decyltetradeceth-24 | 0.2 | 0.2 | 0.3 | 0.3 | 0.3 | 0.3 |
| Tranexamic acid | 2 | 2 | 2 | 2 | 2 | 2 |
| Citric acid | Proper quantity | Proper quantity | Proper quantity | Proper quantity | Proper quantity | Proper quantity |
| Sodium citrate | Proper quantity | Proper quantity | Proper quantity | Proper quantity | Proper quantity | Proper quantity |
| Disodium edetate | Proper quantity | Proper quantity | Proper quantity | Proper quantity | Proper quantity | Proper quantity |
| Na pyrosulfite | Proper quantity | Proper quantity | Proper quantity | Proper quantity | Proper quantity | Proper quantity |
| Phenoxy ethanol | Proper quantity | Proper quantity | Proper quantity | Proper quantity | Proper quantity | Proper quantity |
| Perfume | Proper quantity | Proper quantity | Proper quantity | Proper quantity | Proper quantity | Proper quantity |
| Total | 100 | 100 | 100 | 100 | 100 | 100 |
| Absence of stickiness when drying | B | A | A | B | B | D |
| Freshness | B | B | B | B | B | B |
| Rich texture | B | A | A | A | A | A |
| Skin softness | B | A | A | A | B | C |
| Smooth and dry feel | B | A | A | B | B | D |
| Sliminess | B | B | B | B | B | D |
| Appearance (color) over time | B | B | B | B | B | B |
| Viscosity (mPa·s) | 10 | 10 | 10 | 230 | 280 | 680 |

TABLE 3

| Name of raw materials | Example 6 | Comparative Example 5 |
|---|---|---|
| Purified water | Balance | Balance |
| Ethanol | 4 | 4 |
| Glycerin | 3 | 3 |
| Dipropylene glycol | 5 | 5 |
| PEG/PPG-14/7 dimethyl ether | 3 | 3 |
| Carboxymethylcellulose | 0.8 | 0.8 |
| Alkyl-modified carboxy vinyl polymer | — | 0.1 |
| Tranexamic acid | 2 | 2 |
| Citric acid | Proper quantity | Proper quantity |
| Sodium citrate | Proper quantity | Proper quantity |
| Disodium edetate | Proper quantity | Proper quantity |
| Na pyrosulfite | Proper quantity | Proper quantity |
| Phenoxy ethanol | Proper quantity | Proper quantity |
| Perfume | Proper quantity | Proper quantity |
| Total | 100 | 100 |
| Absence of stickiness when drying | B | C |
| Freshness | B | C |
| Rich texture | A | B |
| Skin softness | A | C |
| Smooth and dry feel | B | D |
| Sliminess | B | D |
| Appearance (color) over time | B | B |
| Viscosity (mPa·s) | 200 | 1800 |

Although Comparative Example 1 to which tranexamic acid was not added did not cause stickiness, stickiness was caused when tranexamic acid was added (Comparative Example 2), and the stickiness was suppressed when xanthan gum was added thereto but sliminess was rather sensed and notable discoloration occurred over time (Comparative Example 3).

However, in Examples 1 to 5 wherein carboxymethylcellulose was added in place of xanthan gum, not only the stickiness caused by tranexamic acid was suppressed but a good rich texture was also obtained and the skin softness with a smooth and dry feel without sliminess was achieved.

The appearance color over time was also the same as Comparative Example 2 to which tranexamic acid was added. On the other hand, the amount of carboxymethylcellulose to be added exceeded 1.5% by mass, the viscosity was over 500 mPa·s and stickiness and sliminess were sensed (Comparative Example 4).

The effect of the present invention was still obtained even when a hydrophilic amphiphilic substance such as PPG-13 decyltetradeceth-24 was not added (Example 6), but when only 0.1% by mass of an alkyl-modified carboxy vinyl polymer, which is a thickener other than carboxymethylcellulose, was added, the viscosity of the obtained preparation significantly exceeded the range of the invention of the present application (500 mPa·s or less) and sliminess was caused and a smooth and dry feel was lost when used (Comparative Example 5).

Specific numerical values are not shown in Tables but all the compositions of Examples 1 to 6 had an L value of 50 or more when measured using Color-EYE7000 (product of GretagMacbeth GmbH) and were transparent or semitransparent.

Examples 7 and 8, Comparative Examples 6 to 8

The liquid compositions (microemulsion type) having the composition shown in Table 4 below were prepared. The actual application test using these compositions was carried out in the same manner as above, and the compositions were evaluated and ranked based on the same evaluation score criteria. The L value of each composition was also measured using Color-EYE7000 (product of GretagMacbeth GmbH). The results are shown together in Table 4.

TABLE 4

| Name of raw materials | Comparative Example 6 | Comparative Example 7 | Example 7 | Example 8 | Comparative Example 8 |
|---|---|---|---|---|---|
| Purified water | Balance | Balance | Balance | Balance | Balance |
| Ethanol | 4 | 4 | 4 | 4 | 4 |
| Glycerin | 3 | 3 | 3 | 3 | 3 |
| Dipropylene glycol | 5 | 5 | 5 | 5 | 5 |
| PEG/PPG-14/7 dimethyl ether | 3 | 3 | 3 | 3 | 3 |
| Xanthan gum | — | 0.02 | — | — | — |
| Carboxymethylcellulose | — | — | 0.02 | 0.02 | 0.02 |
| PEG-30 soy sterol | 0.15 | 0.15 | 0.15 | 2.5 | 2.5 |
| Sorbitan sesquiisostearate | 0.05 | 0.05 | 0.05 | 0.8 | 0.8 |
| Isostearate | 0.3 | 0.3 | 0.3 | 5 | 8 |
| Hydrogenated polydecene | 0.2 | 0.2 | 0.2 | 3 | 4 |
| Tranexamic acid | 2 | 2 | 2 | 2 | 2 |
| Citric acid | Proper quantity | Proper quantity | Proper quantity | Proper quantity | Proper quantity |
| Sodium citrate | Proper quantity | Proper quantity | Proper quantity | Proper quantity | Proper quantity |
| Disodium edetate | Proper quantity | Proper quantity | Proper quantity | Proper quantity | Proper quantity |
| Na pyrosulfite | Proper quantity | Proper quantity | Proper quantity | Proper quantity | Proper quantity |
| Phenoxy ethanol | Proper quantity | Proper quantity | Proper quantity | Proper quantity | Proper quantity |
| Perfume | Proper quantity | Proper quantity | Proper quantity | Proper quantity | Proper quantity |
| Total | 100 | 100 | 100 | 100 | 100 |
| Absence of stickiness when drying | D | B | B | B | B |
| Freshness | D | B | B | B | C |
| Rich texture | D | B | B | B | B |
| Skin softness | C | B | B | B | B |
| Smooth and dry feel | D | D | B | B | D |
| Sliminess | B | D | B | B | C |
| Appearance (color) over time | B | D | B | B | B |
| Viscosity (mPa · s) | 10 | 10 | 10 | 10 | 10 |
| L value | 92 | 91 | 92 | 55 | 30 |

The stickiness caused by adding tranexamic acid (Comparative Example 6) was suppressed by the addition of xanthan gum, however, the sliminess and discoloration over time were caused by xanthan gum failing to achieve a smooth and dry feel (Comparative Example 7). To the contrary, Example 7 to which carboxymethylcellulose was added achieved a smooth and dry feel without stickiness and sliminess and also gave a good rich texture and the skin softness, and did not discolor over time.

Further, when the composition contained a liquid oil component within the range wherein an L value was maintained at 50 or more, all evaluated properties were good (Examples 7 and 8), whereas when a liquid oil component was added in a large amount giving an L value of below 50, a smooth and dry feel was not always achieved (Comparative Example 8).

Formulation Example 1

| Skin softener: | |
|---|---|
| Components | Amount in formula (% by mass) |
| Tranexamic acid | 1.0 |
| Potassium 4-methoxysalicylate | 2.0 |
| Glycerin | 8.0 |
| Butylene glycol | 4.0 |
| Hyaluronic acid | 0.01 |
| Carboxymethylcellulose | 0.05 |
| PEG/PPG-17/4 dimethyl ether | 3.0 |
| PEG-13 decyl tetradecyl ether-24 | 0.2 |
| PEG-10 methyl ether dimethicone | 0.5 |
| Citric acid | Proper quantity |
| Sodium citrate | Proper quantity |
| Sodium metaphosphate | Proper quantity |
| Sodium pyrosulfite | Proper quantity |
| Phenoxyethanol | Proper quantity |

-continued

| Skin softener: | |
|---|---|
| Components | Amount in formula (% by mass) |
| Perfume | Proper quantity |
| Ion-exchanged water | Balance |

Production Method:

The water soluble components were dissolved in a sequential order in ion-exchanged water in accordance with a routine method to prepare a water phase. The water insoluble components, mixed with the amphiphilic component, were then added to the water phase, thereby obtaining a skin softener.

Formulation Example 2

| Semitransparent skin softener (L value: 60) | |
|---|---|
| Components | Amount in formula (% by mass) |
| Tranexamic acid | 3.0 |
| Ethyl vitamin C | 1.5 |
| Dipotassium glycyrrhizinate | 0.05 |
| Glycerin | 1.0 |
| Dipropylene glycol | 4.0 |
| Polyethylene glycol 20000 | 1.0 |
| Carboxymethylcellulose | 0.1 |
| Sorbitan sesquiisostearate | 0.15 |
| Polyoxyethylene phytosterol | 0.5 |
| Isostearyl alcohol | 0.5 |
| Isostearic acid | 0.5 |
| Squalane | 1.0 |
| Citric acid | Proper quantity |
| Sodium citrate | Proper quantity |

Semitransparent skin softener (L value: 60)

| Components | Amount in formula (% by mass) |
| --- | --- |
| Sodium metaphosphate | Proper quantity |
| Sodium pyrosulfite | Proper quantity |
| Methyl paraben | Proper quantity |
| Perfume | Proper quantity |
| Colorant | Proper quantity |
| Ion-exchanged water | Balance |

Production Method:

The water soluble components were dissolved in a sequential order in ion-exchanged water in accordance with a routine method to prepare a water phase. The water insoluble components, mixed with the amphiphilic component with heating, were then gradually added to the water phase, thereby obtaining a semitransparent skin softener.

Formulation Example 3

Essence:

| Components | Amount in formula (% by mass) |
| --- | --- |
| Methylamide hydrochloride tranexamate | 1.0 |
| Glucoside ascorbate | 2.0 |
| Dipotassium glycyrrhizinate | 0.05 |
| Glycerin | 10.0 |
| Propylene glycol | 5.0 |
| Maltitol | 3.0 |
| Xylitol | 2.0 |
| Acetylated hyaluronic acid | 0.03 |
| Carboxymethylcellulose | 1.5 |
| PEG-10 dimethicone | 0.5 |
| Dimethicone | 0.5 |
| PEG/PPG-14/7 dimethyl ether | 1.5 |
| Isostearic acid PEG-20 glyceryl | 0.1 |
| Citric acid | Proper quantity |
| Sodium citrate | Proper quantity |

Essence:

| Components | Amount in formula (% by mass) |
| --- | --- |
| Edetate | Proper quantity |
| Phenoxyethanol | Proper quantity |
| Perfume | Proper quantity |
| Ion-exchanged water | Balance |

Production Method:

The water soluble components were dissolved in a sequential order in ion-exchanged water in accordance with a routine method to prepare a water phase. The water insoluble components were mixed and then gradually added to the water phase and treated using a homogenizer, thereby obtaining an essence.

The invention claimed is:

1. A method of suppressing stickiness and coarseness due to the presence of tranexamic acid or derivatives thereof in a liquid skin-conditioning composition comprising more than 1.0 and up to 5.0% by mass of at least one selected from the group consisting of tranexamic acid and derivatives thereof, the method comprising the step of: combining 0.005 to 1.5% by mass of carboxymethylcellulose with the liquid skin-conditioning composition, whereby the composition has a viscosity of 500 mPa·s or less at 30° C., wherein stickiness and coarseness are reduced upon the combination with carboxymethylcellulose, and wherein carboxymethylcellulose is the sole thickening agent.

2. The method according to claim 1, wherein: the liquid skin-conditioning composition further comprises 30 to 95% by mass of water.

3. The method according to claim 1, wherein: the derivatives of tranexamic acid is methylamide hydrochloride tranexamate.

4. The method according to claim 1, wherein: the liquid skin-conditioning composition is a skin softener or an essence for the purpose of improving rough skin or whitening.

* * * * *